Figure 1:
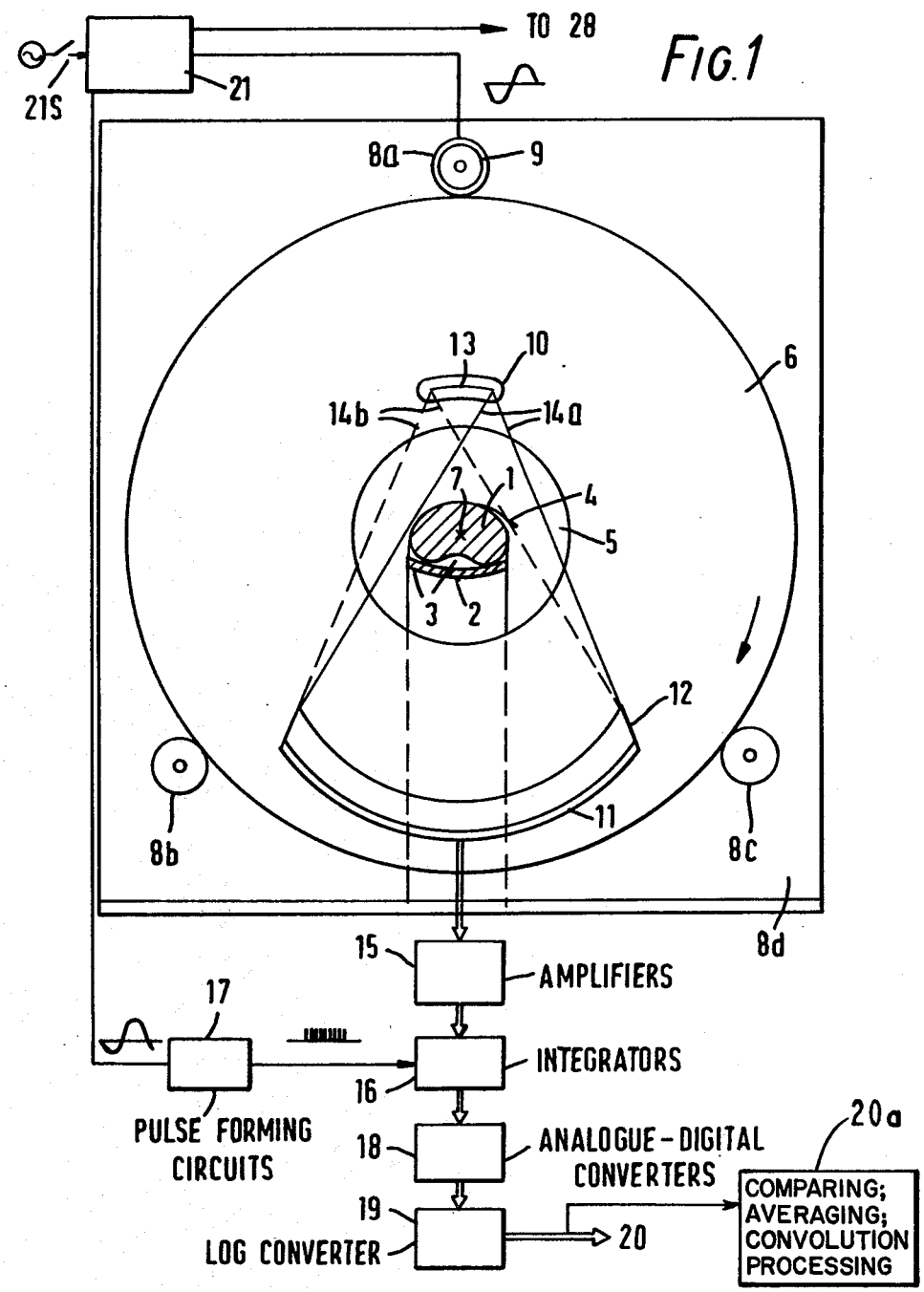

United States Patent [19]

Hounsfield et al.

[11] 4,172,978

[45] Oct. 30, 1979

[54] RADIOGRAPHY

[75] Inventors: Godfrey N. Hounsfield, Newark; Colin C. Oliver, Slough; Stephen R. Bates, Bourne End; Brian H. Lill, Fluckwell Heath, all of England

[73] Assignee: EMI Limited, Hayes, England

[21] Appl. No.: 823,709

[22] Filed: Aug. 11, 1977

[30] Foreign Application Priority Data

Aug. 17, 1977 [GB] United Kingdom ............... 34120/77

[51] Int. Cl.² ............................................. G03B 41/16
[52] U.S. Cl. .................................. 250/445 T; 250/360
[58] Field of Search ........................... 250/445 T, 360

[56] References Cited

U.S. PATENT DOCUMENTS 4,010,370  3/1977  LeMay ............................. 250/445 T

Primary Examiner—Craig E. Church
Attorney, Agent, or Firm—Cooper, Dunham, Clark, Griffin & Moran

[57] ABSTRACT

In a computerized tomographic apparatus, different detectors are caused to receive radiation along substantially the same beam path through the body in order to permit the evaluation of differences in performance of the detectors. This evaluation is average with other evaluations made in respect of the same detector for other beam paths so as to reduce the risk that erroneous performance differences may be evaluated in the event that any of the relevant beam paths lies adjacent a bone edge in a patient's body. Also disclosed are techniques for electronically deflecting the radiation so that part at least of the radiation is taken clear of the body and can be detected to provide reference signals.

8 Claims, 3 Drawing Figures

RADIOGRAPHY

The present invention relates to radiography, and it relates especially to that branch of radiography which has become known as computerised axial tomography, or briefly C.A.T. The object of performing C.A.T. is to produce a representation of the variation of absorption with respect to penetrating radiation, such as X-radiation, over a cross-sectional region of a patient's body.

Apparatus for performing C.A.T. is disclosed and claimed in U.S. Pat. No. 3,778,614 from which it will be appreciated that the radiation is projected through the patient's body along many pencil-like beam paths traversing the region of interest and that the amount of radiation emergent from the body along each path is detected. Electrical signals indicative of the amounts of radiation so detected are processed in order to produce the desired representation. The aforementioned Patent discloses examples of scanning apparatus which can be used to acquire the absorption data and also an example of a technique for processing the acquired data to produce said representation.

U.S. Pat. Nos. 3,937,963 and 3,946,234 and 4,010,370 and 4,115,698 disclose alternative scanning apparatuses and U.S. Pat. No. 3,924,129 discloses an alternative processing technique.

The present invention has especial, but not exclusive, application to C.A.T. scanners having a scanning apparatus of the kind described in the aforementioned U.S. Pat. Nos. 4,010,370 and 4,115,698. In such apparatus, an x-ray tube is arranged to generate a substantially planar, fan-shaped swath of X-radiation, the swath usually having an angle of about 40° so that it encompasses at least a substantial part of the breadth of the body being examined. The source is caused, by a mechanical driving system, to rotate around the body about an axis intersecting the spread of radiation and a plurality of detectors, which preferably rotate with the source, are disposed to receive radiation emergent form the body along the spread. The X-ray tube has facilities for repetitively scanning the electron beam thereof over the X-ray emitting target/anode thereof, at a rate which is considerably higher than the rate of rotation of the source and detectors around the body. This permits sets of absorption signals relating to the absorption of the radiation in traversing sets of substantially parallel beam paths through the body to be accumulated despite the rotational movement, and moreover, and importantly in a multi-detector arrangement, permits inter-detector sensitivity variations to be allowed for.

The present invention has for one object to provide refinements of the apparatus described in the immediately preceding paragraph.

According to the invention there is provided medical radiographic apparatus including means defining a patient position to be occupied by a cross-sectional slice of the body of a patient, a source of X-radiation mounted to project said radiation through said patient position, means for moving said source angularly around said patient position so as to irradiate said patient position from a plurality of different angular locations, detector means for detecting the radiation emergent from the patient position along a plurality of substantially linear beam paths from each of said locations, said detector means including a plurality of detector devices and the devices being arranged to provide electrical output signals indicative of the radiation detected thereby, processing means for utilising said output signals to evaluate a variable characteristic, with respect to said X-radiation, at each of a number of regions distributed over said slice, means for comparing output signals, derived from first and second detectors and relating to substantially the same beam path, to obtain a comparison signal indicative of differences between the performances of the detectors, means for averaging said comparison signal with other comparison signals relating to the same two detectors and obtained in relation to other beam paths viewed by both detectors to obtain an averaged comparison signals, and means for utilising said averaged comparison signal to reduce the effects of said differences in performance upon the accuracy of said evaluation.

Preferably the source of X-radiation comprises an X-ray tube having an elongated target over which an electron beam can be deflected repetitively during said angular movement and the deflection is sufficient to take at least some of the radiation clear of the body slice at reference times during the examination. Preferably also reference attenuator means are included and disposed to be irradiated by said radiation during said reference times to permit the production of reference signals indicative of the over-all performance of the scanner.

In order that the invention may be clearly understood and readily carried into effect, one embodiment thereof will now be described, by way of example only, with reference to the accompanying drawings, of which:

FIG. 1 shows, in schematic form and end elevational view, a rotation-only scanner with beam deflection as described in the aforementioned U.S. Pat. No. 4,010,370.

Figure 2:
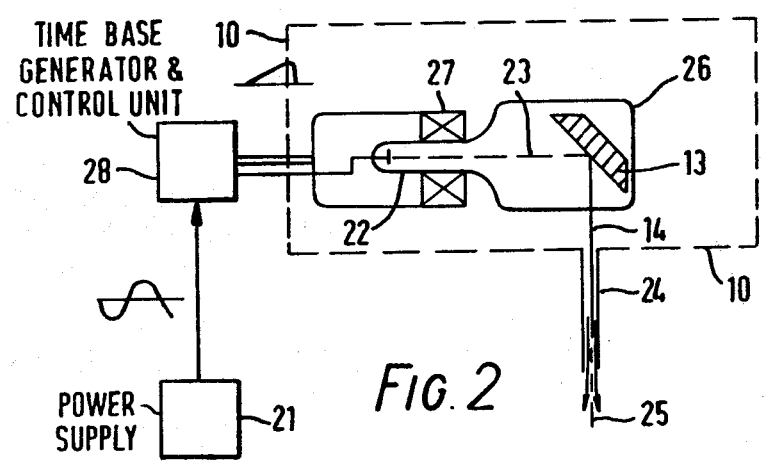
Figure 3:
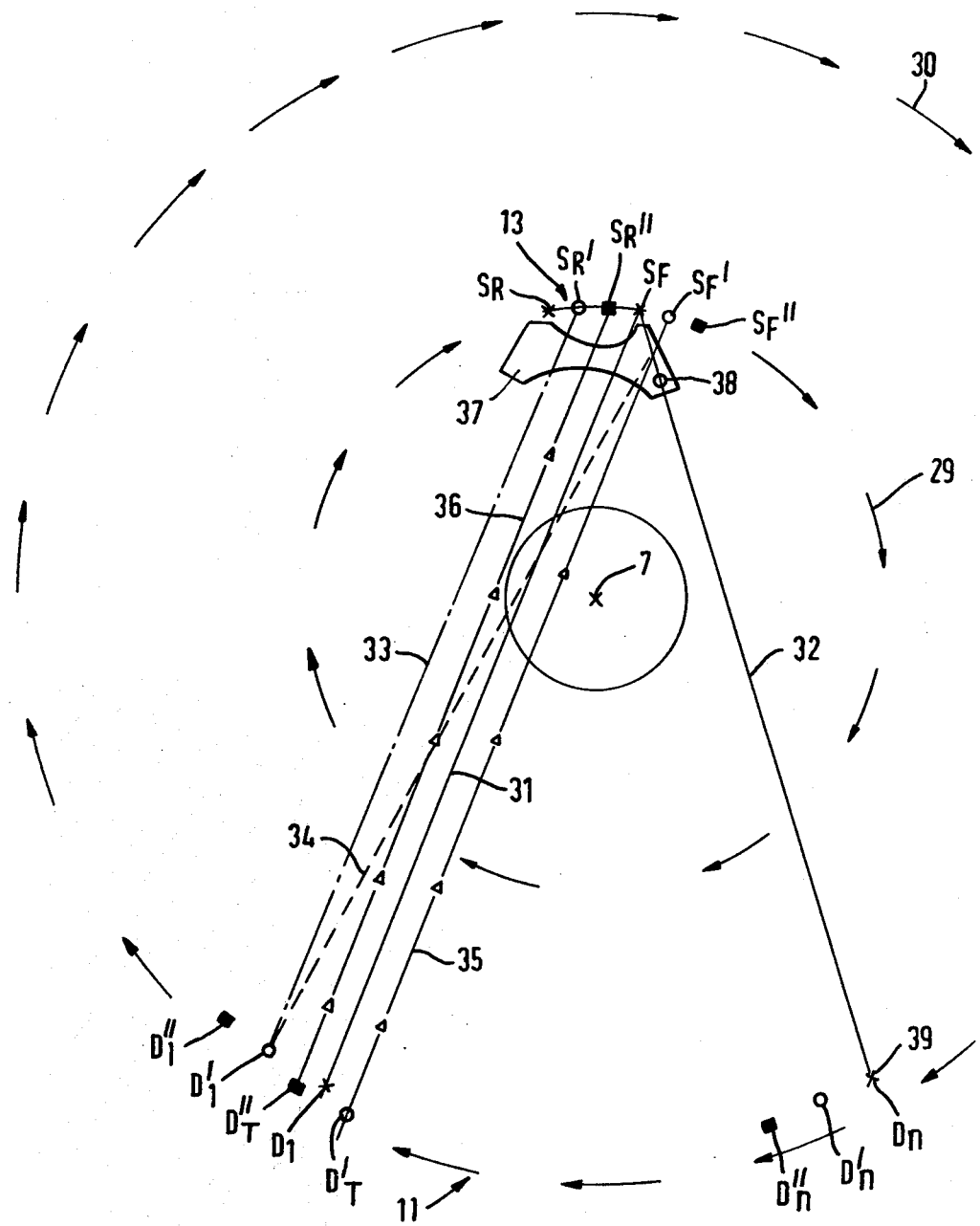

FIG. 2 shows an X-ray source and some control circuits for use with the scanner shown in FIG. 1, and FIG. 3 shows some beam paths irradiated by a scanner of the general kind shown in FIG. 1, and is used in explaining one aspect of the invention.

Referring now to the drawings, FIG. 1 shows a rotation-only scanner with beam deflection.

A body 1 to be examined, shown in transverse section, is supported on a suitably shaped bed 2, also shown in transverse section. A material 3, having an absorption to the radiation similar to that of body tissue, is positioned between the body 1 and the bed 2, to substantially exclude air from the gap therebetween, and is extended partly about the body to provide an approximately circular cross-section to the radiation. The body is retained firmly in the desired position by means such as a retaining strap 4. If desired a more rigid retaining ring, such as the two part ring described in U.S. Pat. No. 3,937,963 may be used.

The bed 2 and the body 1 are inserted into an aperture 5 in a rotatable member 6 so that a desired part of the body is centred in the aperture. The rotatable member 6 is arranged to rotate about an axis 7, longitudinal of the body 1 and perpendicular to the paper, central to the aperture 5. For that purpose it is supported by three gear wheels 8a,b,c, which engage with gear teeth, not shown, cut into the periphery of member 6. The gear wheels 8 are journalled in a main frame 8d of the apparatus which may take any form suitable to support the apparatus and to allow the necessary rotation. Gear wheel 8a is driven by a synchronous electric motor 9, also mounted on the main frame, the operation of which will be described hereinafter.

The rotatable member 6 also carries a source of X-rays 10, a bank of detectors 11 and associated collimators 12. The detectors, which in a typical embodiment number 400, can be of any suitable kind, for example scintillation crystals with associated photomultipliers or photodiodes.

The source 10 includes an elongated target/anode 13, which will be discussed further hereinafter, and provides a fan shaped spread 14 of X-rays from a substantially point origin which can be scanned by electronic means from the position 14a to the position 14b shown. In this example the corresponding scan of the substantially point origin of the X-rays along target 13 is of the order of 5 cm although it may be more or less than this if desired. The collimators have longitudinal axes which intersect at the centre of the anode 13, the axes being angularly spaced by about 1/6° from each other.

In this example the X-ray source 10 is placed of the order of 40 cm from the central axis 7 with the detectors 11 being placed a further 80 cm. on the opposite side of axis 7 so as to intercept the radiation of fan 14 for any position of the point of origin of the X-rays in its lateral scan along target 13. The detectors and source preferably lie along arcs of a single circle which, in this example, is not concentric with axis 7. It should be understood that collimators 12 are of dimensions which allow such interception while preventing the reception of scattered reception to the greatest degree practically possible. Although in the example the distance between source 10 and axis 7 is half of that between detector 11 and axis 7, the relationship is not critical and is chosen in practice with the object of satisfying various design and technical criteria. Thus in one practical example, the source-to-axis distances are 60 cm and 100 cm respectively. Alternatively of course, the source and detectors may be placed equidistant from the axis or in any other desired relationship.

Disregarding for the moment the rotary motion referred to hereinbefore, the arrangement is such that the point of origin of the X-rays is scanned steadily along target 13, taking the fan of X-rays from 14a to 14b, and is rapidly returned to the starting point before repeating the scan. During the time of one such scanning movement each detector of array 11 provides an output indicative of the intensity of radiation received thereby. These outputs are amplified in amplifiers 15 and then applied to integrators 16. There the outputs are integrated over periods determined by a series of pulses from pulse forming circuits 17. In this example the timing of the pulses is such that there are fifty integration periods in the time of one lateral scan of X-ray fan 14 from 14a to 14b. Thus each detector measures radiation in effect along fifty narrow beams joining that detector with fifty equally spaced positions along target 13.

Hereinafter the word "beam" will be used to denote a beam of radiation incident on a detector and scanned with the source and detectors. Conversely the path through the body irradiated by a beam, and fixed in relation to the body, will be termed a "beam path". The paths are, of course, of width determined at least in part by the integration intervals and are of a shape determined by the geometry of scanning movements in those intervals. For the purposes of illustration, however, they may be considered to be represented by single lines which are in fact their centre lines. The lines illustrating the extremes of fan 14 are, in fact, the centre lines of the extreme beams of the fan. Signals representing the intensity the intensity of radiation received along such paths are converted to digital form in converters 18 and to logarithmic form in converters 19 for output at 20 for further processing such as comparing, averaging and convolution processing at 20a, as discussed in more detail below. It will be understood that one amplifier 15, integrator 16, A/D converter 18 and log converter 19 is provided for every detector, all operated in synchronism. The processing is, in one example, effective to sort the signals into sets representing absorption along sets of parallel paths, as will be further explained hereinafter, for processing by a suitable method such as that described in the aforementioned U.S. Pat. No. 3,924,129 to provide the desired representation. The circuits 15 to 19 are of well known construction.

In order to achieve the effect of the present invention, which will be described in detail hereinafter, motor 9 provides a continuous motion of rotatable member 6, and all the equipment mounted thereon, in the clockwise direction, shown by the arrow, about axis 7 and therefore about the body 1 of the patient on bed 2. The rotary motion and the lateral scanning of X-ray fan 14 must be in a strict relationship to achieve the desired result. Synchronous motor 9 is driven by a periodic sinusoidal voltage from a power supply 21 and, after a suitable period of time, stabilises in synchronisation with that sinusoidal voltage. It will be appreciated that, when under load, the motion of motor 9 lags the phase of the sinusoidal voltage but this is not significant provided the load does not change and therefore the lag is constant. The sinusoidal voltage from supply 21 is supplied to a time base generator 28 (FIG. 2) where it provides a periodic sawtooth waveform voltage, to operate the scanning of source 10, and also to unit 17 which converts it to square pulses of the same phase and generates therefrom the series of pulses, in strict phase relationship with the sinusoidal voltage, to clear and read integrators 16 as explained hereinbefore. Pulse forming circuit 17 operates in a conventional manner by any suitable means known in the art. Flyback of the sawtooth waveform takes place during selected groups of resetting periods of the integrators.

The X-ray source 10 is shown in greater detail in FIG. 2 and in this example comprises an electron gun 22, powered by a conventional supply not shown, providing a beam of electrons 23 which is incident on target/anode 13 to provide X-ray fan 14. In FIG. 2 the elongation of target 13 is perpendicular to the paper so that the X-ray fan 14 is also perpendicular to the paper. Source collimator 24 is provided, as shown, to restrict the X-rays substantially to the plane of the fan, shown dotted at 25 and that is then the plane of a section of the body 1 to be examined. The electron gun and target are enclosed in an evacuated envelope 26 having a neck section around which are disposed scanning coils 27. In operation, a suitable time (to allow motor 9 to settle in speed) after power supply 21 is switched on by switch 21s in FIG. 1, the time base generator 28 is switched on by a delayed signal from power supply 21. This signal also switches on electron gun 22. The sawtooth voltage from generator 28 scans the point of incidence of the electron beam 23 along target 13 from one end in a direction perpendicular to the paper to scan the X-ray point as shown in FIG. 1. Although a pencil beam of electrons is indicated it will be understood that it may be a ribbon shaped beam used in conjunction with a suitable shape of target 13. Furthermore oil cooling of target 13, although not shown, is preferably provided in conventional manner. Although scanning coils have been shown in FIG. 2, deflection plates may be used if desired; any configuration of source 10 capable of achieving the scanning of the X-ray fan 14 being suitable for use with the invention. Alternatively any other suitable arrangement for scanning the X-ray fan, in accordance with the principles outlined herein, may be employed.

As described hereinbefore, time base generator 28 provides the scanning sawtooth voltage in conventional manner in phase with the sinusoidal voltage provided by synchronous motor power supply 21 and this maintains the desired relationship between lateral scan and rotary motion. The exact relationship obtained is determined by the gearing of motor 9, turning member 6 through a predetermined angle for each cycle of the sinusoidal voltage. Since the sinusoidal voltage is also supplied to pulse forming circuits 17, the integration times are retained in the desired relationship with the scanning of X-ray fan 14 to provide the required effective beam paths.

It has been mentioned that processing, suitable for use with X-ray apparatus of the type described, such as that disclosed in U.S. Pat. No. 3,924,129 operates preferably on data representing the absorption along a plurality of sets of parallel beam paths in the plane of examination. The manner in which the present invention provides such data, despite the continuous orbital motion involved will now be described with reference to FIG. 3.

Using, where appropriate, the nomenclature of FIG. 1, it will be seen that the source anode 13 and the central detector of the detector array 11 are arranged to rotate, about the axis 7, along respective circular loci 29 and 30; the diameter of circle 30 being twice that of the circle 29. The position occupied by the patient's body 1, of course, has to be wholly within the circle 29. In an initial position of the source 13 and detectors 11 relative to the body, it is assumed that the anode 13 lies on its locus circle 29 within the bounds occupied by the two crosses $S_F$ and $S_R$ (source front and source rear) with respect to the direction of rotation about axis 7, which direction is clockwise in this example. The corresponding position of the bank of detectors 11 is denoted by the two crosses $D_1$ and $D_n$, these letters indicating the first and last detectors in the bank respectively, with respect to the clockwise direction of rotation. It will be appreciated that the detectors $D_1$ and $D_n$ do not lie on the circle 30 because the latter is the locus of the central detector of array 11 only. The array is curved on a radius which is the mean of the radii of the circles 29 and 30. The anode/target 13 is likewise curved, but because of its short length, the departure from the curvature of circle 29 is not evident in the drawing.

In this position, and assuming the electron beam of the source tube to be fully deflected to the right so that the radiation is emitted from $S_F$, the fan of radiation as incident upon the detector bank 11 is shown by the lines 31 and 32, joining $S_F$ to $D_1$ and $D_n$ respectively. The line 31 will be considered as a first beam path of a set of parallel beam paths to be investigated by the apparatus. It will be appreciated that the other detectors in the bank 11 will investigate respective paths of different parallel sets.

The source 13 and detector array are now assumed to rotate smoothly about the axis 7; the electron beam of the tube being periodically deflected along the anode thereof in the opposite direction to the movement of the source as has been previously described. The arrangement is such that if the angle subtended by the source anode 13 at the axis 7 is $3\theta$, then after a rotational movement of $\theta$ by the anode, taking it to the position marked by circles $S_F'$ and $S_R'$, the electron beam has swept to the left-hand end of the anode, i.e., to $S_R'$. Of course, whilst the source has been moving through the angle $\theta$, the detectors have been doing likewise, thus adopting the position bounded by circles $D_1'$ and $D_n'$. Clearly, at this time, the source position is at $S_R'$ and it will be observed that a line 33 joining the positions $S_R'$ and $D_1'$ is parallel to the line 31 joining $S_F$ to $D_1$. Thus it can be seen that, during movement of the source and detector through a first angle $\theta$ about the axis 7, the first detector (in moving from $D_1$ to $D_1'$) provides output signals relating to several (e.g. fifty) parallel beam paths between and including the lines 31 and 33. The number of beam paths is determined, as previously described, by the number of integration intervals during the time taken for the aforementioned rotation of $\theta°$ to occur.

The electron beam is next arranged to fly back rapidly to the right-hand end of the anode 13, and for simplicity it is assumed that the flyback can be regarded as occurring instantaneously so that the source position effectively changes from $S_R'$ to $S_F'$ without appreciable rotation of the source and detectors about the axis 7. In this position, as shown by a dashed line 34, the line linking the first detector at position $D_1'$ to the source at position $S_F'$ is no longer paralleled to the lines 31 and 33. Thus the first detector will now proceed to product output signals relating to another set of beam paths. However another detector in the bank 11, namely the T'th detector, which is then disposed at a position marked by a circle $D_{T'}$, receives radiation from the source at position $S_F'$ along a line 35 which is parallel to the lines 31 and 33. Thus during movement of the source and detectors through a second angle $\theta$ about axis 7, to the position indicated by squares marked $S_F''$ and $S_R''$, and the corresponding deflection of the electron beam of the tube from one end to the other of the anode, the T'th detector provides output signals which relate to more component paths of the set previously investigated by the first detector.

As can be seen, at the end of the second angular rotation of $\theta$, the T'th detector assumes the position marked by a square $D_T''$ (the positions at that time occupied by the first and last detectors being marked by squares $D_1''$ and $D_n''$ respectively). The source position at this time is marked by a square $S_R''$ and it will be seen that a line 36 linking $S_R''$ to $D_T''$ is parallel to the lines 31, 33 and 35. Thus the beam paths investigated by the T'th detector during the second rotational movement of $\theta$ are disposed between, and include, the lines 35 and 36.

It will be observed that there is a substantial amount of overlap between the area bounded by the lines 31 and 33 and that bounded by the lines 35 and 36. This is important because it allows the performances of the first and the T'th detectors to be compared in relation to beam paths, occurring in the overlap region, when the two detectors should provide substantially the same output signals as one another. Clearly, with further rotation, further detectors will contribute output signals relating to the same parallel set of beam paths, and a region of overlap will occur at each change from one detector to another, thus permitting the detector performances to be normalised to that of the first detector by techniques of successive comparison.

Of course, other detectors in the array 11 are at the same time producing output signals relating to beam paths in other parallel sets and after a total rotation of about 220° (i.e., 180° plus the angle subtended at the mid-point of the source anode 11 by the detector array 11—in this example 40°) a large number of sets of parallel beam paths distributed across the body 1, each set being at a respective angle to the body in the plane of investigation, have been investigated, the sets being distributed over 180°.

As can be seen in FIG. 3, it is preferable for the body 1 to be so positioned in relation to the source and detectors that, at least at some times during the examination, one or more detectors (e.g. the n'th detector as shown) receive radiation, from the source, which has not traversed the body. Line 32, for instance, represents such a case. In accordance with one aspect of this invention, a suitably shaped attenuator member formed of carbon, for example, is disposed to be irradiated by radiation projected along paths such as 32 and is arranged to attenuate the radiation by an amount similar to the mean attenuation suffered by the radiation on traversing the body. This permits a reference reading, indicative of the absolute performance of the relevant detector (the n'th detector in this case) to be obtained.

A suitable attenuator is shown at 37 in FIG. 3; the attenuator 37 in this case being shaped to tend to compensate for the different path lengths traversed by the radiation through the body at different lateral positions thereacross. The attenuator could comprise, however, merely two portions outside the region occupied by the body. Attenuator 37 rotates with the source 13 around the axis 7. In a refinement of this arrangement, a lamp 38, sited on the attenuator, and a photocell 39, co-sited with the relevant detector, both lamp 38 and detector 39 being outside the plane of radiation, are used to indicate whether the patient's body is intruding into the path of radiation, thus rendering the reference readings unsuitable for use. As long as a direct line of sight exists between the lamp 38 and the photocell 39, the reference readings obtained are suitable for use.

The zero level and degree of phosphorescence in the detectors can be checked by interrupting the radiation during the aforementioned flyback periods. To give an understanding of the times involved, a complete circular scan around the body is typically effected in one second and, if the scanned length of anode 13 is 5 cm., the deflection frequency of the electron beam is about 200 Hz, or 400 Hz if the scanned length of said anode is 2½ cm. The flyback period is typically one-tenth of the forward deflection time. It will be appreciated, therefore, that the amount of overlap between lines such as 31 and 36 is reduced because of the time taken for flyback to be affected. The X-radiation can be interrupted during flyback by switching off the electron beam of the tube or by deflecting said beam away from the anode and on to a suitably positioned absorbing, non X-ray emissive plate or other electrode.

It can occur in some circumstances that the comparison between two detectors (e.g. the first and the T'th detectors) in the region of overlap at a particular angle, say that between lines 31 and 36, can be contaminated by virtue of the existence of a sharp bone edge, or other discontinuity in the body, if the corresponding paths for the two detectors, which should be identical, are disposed just to either side of the edge, or other discontinuity as the case may be. This problem can be alleviated, in accordance with one aspect of the invention, by averaging comparisons between the same two detectors obtained from several parallel sets. For example, the comparison obtained from the first and the T'th detectors in the region between lines 31 and 36 would not be used alone, but after averaging with corresponding comparison values from other angles, e.g. parallel to line 34.

In practice, a set of parallel paths distributed laterally across the body may be obtained from a total of twelve detectors.

It is not necessary for the beam paths which are compared to be parallel, or for them to fully overlap one another. Provided that different detectors receive radiation projected through the body along substantially similar beam paths, sufficiently accurate comparisons can be made, especially bearing in mind that individual comparisons are not used in isolation for normalisation of detector performance characteristics. Rather, the detector performance normalisation is carried out on the basis of the average of a number of individual comparisons. The individual comparisons may, as the example described above, relate to paths at different angles in the body, or they may relate to parallel paths such as those in the region between the lines 31 and 36 in FIG. 3. As mentioned before, the beam paths used for the individual comparisons need not fully overlap.

It will be appreciated that the individual comparisons could be evaluated for each relevant beam path and then the average comparison value produced by adding the individual comparisons and dividing by the number of comparisons. Alternatively, of course, the radiation readings for the individual beam paths could be summed separately for the two detectors concerned and then the comparison evaluated as the difference between the two sums.

It is stressed that the particular relationship between the electron beam deflection of the tube 10 and the rotation of member 6 and its attachments is not of importance so far as this invention is concerned. The relationship may be such as to cause adjacent beam paths to be non-parallel in accordance with the teachings of the aforementioned U.S. Pat. No. 4,115,698.

Additionally, it is not necessary for the detector comparison and averaging to be effected over the whole of the investigated region. It may be effected, for example, only over the central part of the body 1.

As previously mentioned, the detector array 11 can contain many detectors. In one practical embodiment using a 40° fan of radiation, four hundred detectors are used. The resolution of all the detectors need not be the same, however, and preferably 240 high resolution detectors are used in the central 20° of the fan, a further 120 detectors being used to cover the 10° either side of the central region; 20 low resolution detectors being disposed to either side of the fan outside these detectors for reference purposes.

In these circumstances it will be appreciated that the beam paths investigated by adjacent detectors do not differ greatly from one another, particularly when it is taken into account that, for the high resolution detectors at least, the number of integration intervals per lateral beam deflection period can be increased to over one hundred. Thus, in order to reduce the amount of information to be processed, it can be convenient to combine output signals from adjacent detectors and relating to closely angled beam paths, which intersect in a central region of the body 1. This can be achieved, for example, by means of a form of the apparatus described with reference to FIGS. 5-8 inclusive of U.S. patent application No. 698,047 filed June 21, 1976 (now U.S. Pat. No. 4,066,900). In essence, the combination of output signals is arranged to produce signals relating to beam paths which are "waisted", i.e., they are narrower in the centre of the body 1 than at the edges thereof.

The combination of output signals from adjacent detectors referred to thus far has assumed that combined signals relate to beam paths which are inclined to one another but are disposed at a substantially constant perpendicular distance from the axis of rotation (7 in FIG. 1). This need not necessarily be the case, however, and in some circumstances the combined signals may relate to beam paths which are not only inclined to each other but are disposed at different perpendicular distances from said axis 7. This can be done in order to select a suitable reduction for the scanner, either in all portions of the fan or in some selected regions thereof, and is achieved by suitable timing and delay operations.

As thus far described, the investigated region of the body has been a substantially planar region perpendicular to the axis of rotation of the scanner. However if desired the apparatus can be used to examine slanting slices through the body, or volumetric regions thereof, using the scanning techniques described in U.S. patent application Ser. No. 790,474 filed Apr. 25, 1977, and U.S. patent application Ser. No. 816,686, filed July 18, 1977.

Moreover, in order to reduce the irradiation of the patent and to reduce the effects of scattered radiation, it is possible to use, either in a source of collimator or in a detector collimator or both, one or more baffles substantially parallel to the plane of radiation as described in U.S. patent application Ser. No. 726,050 filed Sept. 23, 1976.

Instead of deriving the timing pulses as described with reference to FIG. 1, it is preferable in some cases to use a graticule, secured to the member 6, so as to rotate therewith past a photocell and detector arrangement of known kind. In this case, the drive for the member 6 and its attachments can be simplified and can compromise, for example, a belt driven by an electric motor and passing round a suitable annular flange attached to the member 6.

What we claim is:

1. Medical radiographic apparatus including means defining a patient position to be occupied by a cross-sectional slice of the body of a patient, a source of X-radiation mounted to project said radiation through said patient position, means for moving said source angularly around said patient position so as to irradiate said patient position from a plurality of different angular locations, detector means for detecting the radiation emergent from the patient position along a plurality of substantially linear beam paths from each of said locations, said detector means including a plurality of detector devices and means to provide electrical output signals indicative of the radiation detected by said detector devices, processing means for utilising said output signals to evaluate a variable characteristic, with respect to said X-radiation, at each of a number of regions distributed over said slice, means for comparing output signals, derived from first and second detectors and relating to substantially the same beam path, to obtain a comparison signal indicative of differences between the performances of the detectors and means for averaging said comparison signal with other comparison signals relating to the same two detectors and obtained in relation to other beam paths viewed by both detectors to obtain an averaged comparison signals, and means for utilising said averaged comparison signal to reduce the effects of said differences in performance upon the accuracy of said evaluation.

2. Apparatus according to claim 1 wherein the source of radiation comprises an X-ray tube having an elongated target, means for generating an electron beam and means for repetitively deflecting said electron beam to and fro along said target during said angular movement.

3. Apparatus according to claim 2 wherein said means for causing radiation projected along at least some of said paths to be detected by different detectors comprises, in combination, said means for repetitively deflecting and a mounting structure mounting said source and said detector means relative to an axis intersecting said patient position to maintain said source on the one hand and said detector means on the other hand at different distances from said axis during said angular movement.

4. Apparatus according to claim 2 wherein the deflecting means include means for deflecting said electron beam to an extent sufficient to take at least some of the radiation clear of the body slice at reference times during the angular movement.

5. Apparatus according to claim 4 including reference attenuator means disposed to be irradiated by said radiation during said reference times to permit at least one of said detector devices to produce reference signals.

6. Apparatus according to claim 5 including a light source and a photodetector, one mounted adjacent said reference attenuator means and one mounted adjacent said at least one detector device to establish a line-of-sight control arrangement wherey said reference signals can be rejected as unsuitable for use in the event that said line of sight is interrupted.

7. Apparatus according to claim 1 wherein said processing means comprises circuits and devices for effecting convolution processing of said output signals or of signals derived therefrom.

8. Apparatus according to claim 1 wherein said x-radiation conforms to a substantially fan-shaped distribution.

* * * * *

UNITED STATES PATENT AND TRADEMARK OFFICE
CERTIFICATE OF CORRECTION

PATENT NO. : 4,172,978
DATED : October 30, 1979
INVENTOR(S) : GODFREY N. HOUNSFIELD, COLIN C. OLIVER, STEPHEN R. BATES and BRIAN H. LILL It is certified that error appears in the above-identified patent and that said Letters Patent are hereby corrected as shown below:

Under FOREIGN APPLICATION PRIORITY DATA, delete "August 17, 1977" and "34120/77", respectively, and insert -- August 17, 1976 -- and -- 34120/76 --, respectively.

ABSTRACT, line 5, delete "average" and insert -- averaged --.

Column 6, line 28, delete "product" and insert -- produce --.

Signed and Sealed this

Eighth Day of July 1980

[SEAL]

Attest:

SIDNEY A. DIAMOND

Attesting Officer

Commissioner of Patents and Trademarks